(12) United States Patent
Beck et al.

(10) Patent No.: US 6,546,283 B1
(45) Date of Patent: Apr. 8, 2003

(54) HIGH CURRENT DENSITY IONTOPHORETIC DEVICE AND METHOD OF USE THEREOF

(75) Inventors: Jon E. Beck, Salt Lake City, UT (US); Lindsay B. Lloyd, Salt Lake City, UT (US)

(73) Assignee: Iomed, Inc., Salt Lake City, UT (US)

( * ) Notice: Subject to any disclaimer, the term of this patent is extended or adjusted under 35 U.S.C. 154(b) by 0 days.

(21) Appl. No.: 09/691,411

(22) Filed: Oct. 18, 2000

(51) Int. Cl.[7] ................................................ A61N 1/30
(52) U.S. Cl. ........................ 604/20; 604/501; 424/427
(58) Field of Search ........................... 604/20, 22, 501, 604/294, 289; 424/447, 449, 427

(56) References Cited

U.S. PATENT DOCUMENTS

| | | | |
|---|---|---|---|
| 542,508 A | 7/1895 | Van Tuyl, Jr. | |
| 2,525,381 A | 10/1950 | Tower | 604/20 |
| 3,122,137 A | 2/1964 | Erlanger | 604/20 |
| 4,564,016 A | 1/1986 | Maurice et al. | 128/645 |
| 4,955,378 A | 9/1990 | Grasso | 128/421 |
| 5,032,110 A | 7/1991 | Watanabe | 604/20 |
| 5,053,000 A | 10/1991 | Booth et al. | 604/20 |
| 5,169,384 A | 12/1992 | Bosniak et al. | 604/20 |
| 5,174,304 A | 12/1992 | Latina et al. | 128/793 |
| 5,674,196 A | 10/1997 | Donaldson et al. | 604/93 |
| 6,101,411 A | 8/2000 | Newsome | 604/20 |
| 6,154,671 A | 11/2000 | Parel et al. | 604/20 |
| 6,319,240 B1 * | 11/2001 | Beck | 604/501 |

FOREIGN PATENT DOCUMENTS

DE     27 37 665 A1     3/1979

* cited by examiner

Primary Examiner—Edward K. Look
Assistant Examiner—Kimya N McCoy
(74) Attorney, Agent, or Firm—Factor & Pariners

(57) ABSTRACT

A high current density iontophoretic device, comprising a reservoir, an applicator, an orientation maintaining member and an iontophoretic medicament administering member. The reservoir is capable of retaining medicament. The applicator is positionable upon a surface of an eye and includes at least one punctation therethrough. The at least one punctation is capable of being placed in fluid communication with each of the reservoir and at least one treatment area of an eye upon operative positioning of same. The orientation member substantially maintains the orientation of the applicator in the desired orientation upon operative positioning of same. The iontophoretic administering member serves to administer a medicament from the reservoir to the at least one punctation and, in turn, to a specific region of an eye of a patient.

7 Claims, 2 Drawing Sheets

HIGH CURRENT DENSITY IONTOPHORETIC DEVICE AND METHOD OF USE THEREOF

BACKGROUND OF THE INVENTION

1. Field of the Invention

The present invention relates in general to an iontophoretic device for the administration of an electric current to a soft tissue of a patient, more specifically to an iontophoretic device that is capable of continuous, highly directed application of an electric current to the soft tissue of a patient.

2. Background Art

Iontophoresis is a technique which can be used to transport soluble ions across a body surface or membrane. This technique is based on the principle that an applied electric potential will cause ions to move in a desired manner according to the charge of the ions, the size of the ions, the magnitude of the electrical current or voltage being applied, electrode composition, and duration of the electrical current or voltage. Iontophoresis is an example of a method more generally known as electrotransport, which has been found to be very useful in the transdermal administration of medicine and also in some diagnostic applications.

Iontophoresis has been used to administer medicament to soft tissues of patients, including to the eyes of patients. Such treatments have been successful due to the increased ability of medicine to penetrate the tissue of the patient, and treat the selected area. However, care must be taken in utilizing iontophoresis for the treatment of these soft tissue areas. The application of an electric current to drive a medicament iontophoretically can have the tendency to burn the area of application if too much electric charge is allowed to pass at too great a rate. Therefore, care must be taken in the amount of electric charge applied over a period of time.

An additional concern in the use of iontophoresis for the treatment of soft tissues is that the application of the electric current to the tissue may treat healthy as well as targeted areas. It has been know in the art to limit the application area of the electric current in order to minimize this effect. Such devices have been formed in portions of an annulus, a complete annulus, or a reduced-size applicator. However, none of these solutions have addressed the need for specific application of electric current to a definite area.

One solution that has addressed the application of electric current to a specified area is the application of medicament utilizing a thin tube filled with the medicament whose end is placed manually on the area to be treated, and manually held in position until treatment is completed. While this solution addresses the need for highly specified application of electric current, such a solution is difficult to administer. Since the tube filled with medicament is held manually, any movement, regardless of magnitude, by the administrator or the patient, may alter or even completely change the area of application.

Therefore, it is an object of this invention to provide for the highly directed application of electric current to a soft tissue of a patient, such as an eye, using iontophoresis.

It is a further object of this invention to insure consistent and constant contact of the electric current to the specified area, without the use of unreliable manual means.

SUMMARY OF THE INVENTION

The invention comprises a high current density iontophoretic device, comprising a reservoir, an applicator, means for substantially maintaining orientation of the device and means for iontophoretically administering the medicament from the reservoir. The reservoir is capable of retaining medicament. The applicator is positionable upon a surface of an eye and includes at least one punctation therethrough. The at least one punctation is capable of being placed in fluid communication with each of the reservoir and at least one treatment area of an eye upon operative positioning thereof. The orientation maintaining means maintains the applicator in the desired orientation upon operative positioning thereof. The iontophoretic administering means serves to administer a medicament from the reservoir to the at least one punctation and, in turn, to an eye of a patient.

In a preferred embodiment, the reservoir and the applicator comprise a single unitized member. In other preferred embodiments, the reservoir and the applicator are separate members, and the device further includes a conduit in fluid communication with both the reservoir and the at least one punctation to, in turn, facilitate the remote positioning of the reservoir relative to the applicator. In such embodiments, the conduit is of a substantially circular cross section, and is formed from a flexible material.

In another preferred embodiment, the applicator includes a contact surface and the orientation maintaining means comprising a releasable retaining material associated with the contact surface. In certain embodiments, the releasable retaining material comprises an adhesive. In other embodiments, the releasable retaining material comprises a lightly crosslinked polymer having a tacky surface configuration.

In a preferred embodiment, the device further comprises means for substantially sealing the at least one punctation relative to at least one treatment area. This serves to substantially preclude undesired migration of electric current away from the at least one treatment area. In one such embodiment, the sealing means comprises a raised barrier, associated with the applicator, and at least partially surrounding the at least one punctation. In this embodiment, the applicator comprises a convex shape, to ensure secure contact between the raised barrier and the area surrounding the at least one punctation.

In a preferred embodiment, the at least one punctation is formed in a variety of geometric shapes. Preferably, the shape thereof comprises a circular geometric configuration. It is preferred that the circular geometric configuration includes a diameter of less than 2 mm.

In another preferred embodiment, the applicator is shaped to substantially correspond to the shape of a soft tissue of a patient. In yet another preferred embodiment, the reservoir includes one of a medicament and a medicament carrier, which may comprise a hydrogel medicament carrier.

The invention further comprises a method for treating the eye of a patient comprising the steps of: (a) providing a high current density iontophoretic device; (b) positioning an applicator of the high current density iontophoretic device on the eye of a patient; (c) positioning at least one punctation of the applicator over the portion of the eye requiring treatment; and (d) iontophoretically driving a medicament through the at least one punctation of the applicator of the high current density iontophoretic device.

In a preferred embodiment, the method further comprises the step of retaining the at least one punctation in the desired orientation upon the positioning thereof. In another preferred embodiment, the method further comprises the step of sealing the at least one punctation relative to the surface of the eye, to, in turn, preclude migration of electric current.

DETAILED DESCRIPTION OF THE INVENTION

Figure 1:
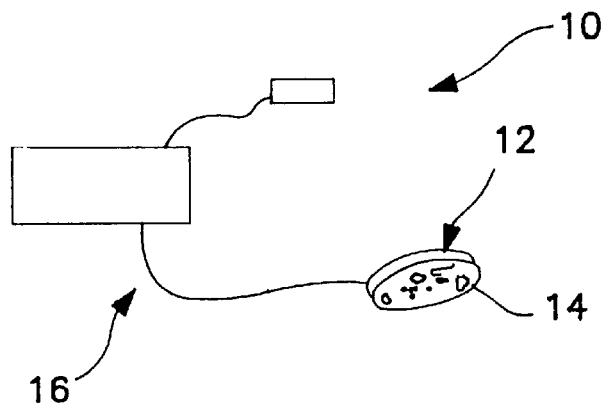
FIG. 1 of the drawings is a schematic view of the device of the present invention.

While this invention is susceptible of embodiment in many different forms, there is shown in the drawings and will be described in detail several specific embodiments with the understanding that the present disclosure is to be considered as an exemplification of the principles of the invention and is not intended to limit the invention to the embodiments illustrated.

High current density iontophoretic device 10 is shown in FIG. 1 as comprising reservoir 12, applicator 14 and means 16 for iontophoretically administering a medicament to an ocular surface such as an eye of a patient. Specifically, punctated iontophoretic device is operatively associated with an eye of a patient for the application of medicament to an eye, to, for example, combat eye infections. Iontophoretic administration means 16 is explained in detail in co-pending application Ser. No. 09/318,181 entitled "Methods and Apparatus for Ocular Iontophoresis" which is incorporated herein in its entirety. Indeed, it will be understood that medicament from the reservoir is driven by an electric current which results from the applying of a potential across two electrodes, one of which may be included in the reservoir, and the other of which may be separate and applicable to another portion of a patient (such as the back of the neck).

Figure 2:
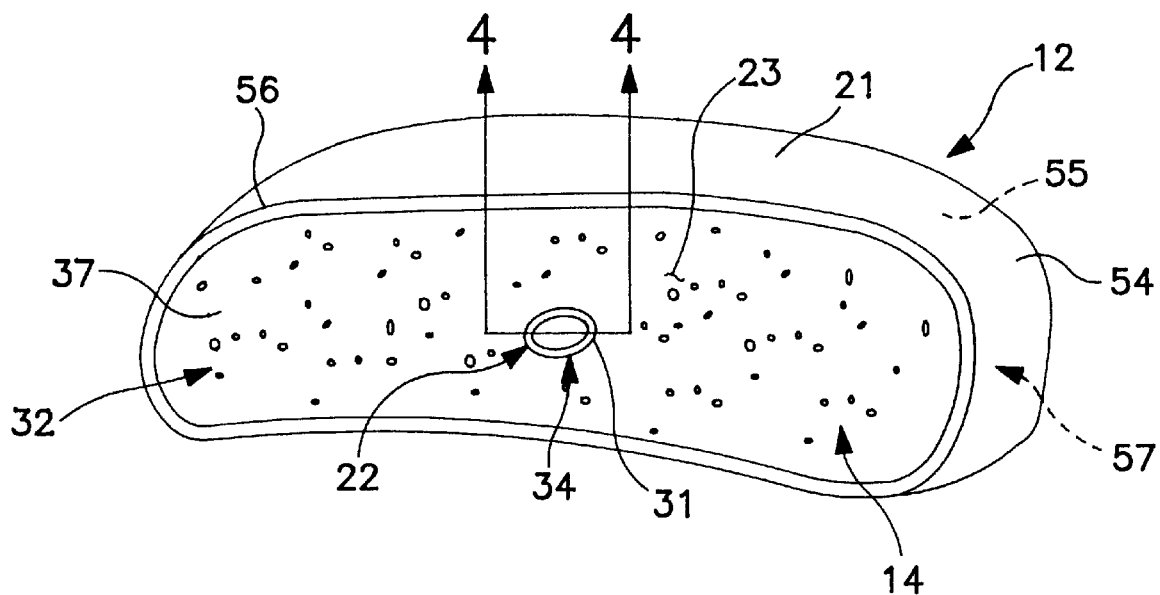
FIG. 2 of the drawings is a perspective view of the applicator of the present invention.

Reservoir 12 is shown in FIG. 2 as comprising shell member 21, that, as will be explained, cooperates with applicator 14 to retain medicament therebetween. Reservoir 12 is generally capable of retaining a medicament in substantial proximity to the soft tissue of a patient's eye for iontophoretic application of that medicament. In particular, shell member 21 of reservoir 12 comprises outside surface 54, inside surface 55, and outer rim 56. Inside surface 55 is formed in such a way as to define a cavity 57. For example, inside surface 55 may be concave. Shell member 21 further is generally formed of a substantially flexible yet impervious material such as, for example, a silicone rubber, to facilitate application on the eye while maintaining secure containment of the medicament.

The medicament that is retained in reservoir 12 may comprise various medicaments and/or medicament carriers in a variety of forms, for example, but not limited to, in aqueous form, in a hydrogel form, or in the form of a hydrated solid, such as, for example, a polymer matrix. Indeed, the device is not limited to use in association with any particular medicament or particular form of medicament carrier.

Applicator 14 is shown in FIG. 2 as comprising at least one punctation, such as punctation 22 which extends through contact surface 23. The applicator is generally associated with rim 56 of shell member 21 of reservoir 12, and serves in part to define cavity 57 formed by shell member 21. Generally, applicator 14 comprises a silicone material, however, other materials including other synthetic and natural compositions are contemplated for use.

Punctation 22 is shown in FIG. 2 as being associated with the applicator in such a way as to place the reservoir and the eye in fluid communication with one another. Such a punctation may be a variety of sizes and shapes depending upon the desired application of the medicament, including but not limited to circular, oval, elliptical, triangular, or other multisided geometric configurations. Preferably, it is contemplated that the punctation comprises a circular configuration which includes an area of about 0.03 $cm^2$. For example, if the soft tissue of an eye is chosen for treatment, and a specific area of the eye is selected, the punctation may be formed specifically to direct the application of a medicament to the particular area. Also, it is contemplated that contact surface 23 may include multiple punctations extending therethrough so that multiple areas of the eye may simultaneously receive treatment.

Contact surface 23 may be in a variety of shapes in area, including, but not limited to, substantially rectangular, circular, or in the form of the whole of or a section of an annulus. Contact surface 23 is configured so as to substantially correspond to the surface configuration of the soft tissue upon which it is applied. In this manner, maximum surface contact of the applicator can be achieved, which, in conjunction with the means for maintaining the desired orientation, assures maximum stability of the device.

Contact surface 23 is shown in FIG. 2 as further comprising means 32 for substantially maintaining desired orientation and means 34 for sealing the at least one punctation relative to the soft tissue surface of the patient. Orientation maintaining means 32 is shown in FIG. 2 as comprising releasable retaining material 37 associated with contact surface 23. Specifically, the material comprises a material that provides for the releasable retention of the punctated iontophoretic device on a soft tissue of a patient, and, in turn, maintains the device in the desired orientation after application and during use.

For example, a weak adhesive may be associated with the contact surface, which adhesive will adhere, at least in part, to the surface which is to be treated. Alternatively, the contact surface may be formed from a relatively lightly cross-linked polymer which includes a tacky configuration lending itself to adherence to the surface which is to be treated. These materials will generally adhere to the surface of the eye. Additionally, these materials are generally removable without damaging the surface of the eye and substantially without leaving residue upon removal. Indeed, many materials are contemplated for use which exhibit the foregoing properties.

Figure 4:
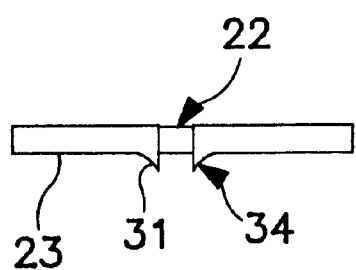
FIG. 4 of the drawings is a partial cross-sectional view of the sealing means, taken generally about lines 4—4 of FIG. 2.

Sealing means 34, as shown in FIGS. 1 and 4, serves to seal the at least one punctation relative to at least one treatment area by substantially precluding the undesired migration of electric current away from at least one punctation 22. As shown in FIG. 4 in detail, sealing means 34 comprises raised barrier 31 associated with punctation 22. It is contemplated that raised barrier 31 is capable of surrounding the entire punctation. However, in certain embodiments, the sealing means will generally prevent migration for only a portion of the area surrounding the punctation. Raised barrier 31 is generally manufactured from a flexible but waterproof material such as, for example, a silicone material, or another rubber or plastic material. In certain embodiments, the raised barrier may be integrated with surface 21. In other embodiments, the orientating means may additionally comprise a sealing means. Specifically, the material used to maintain the device in the proper orientation may likewise include properties which facilitate the sealing of the punctation.

To utilize the device, the administrator (doctor, assistant, etc.) first selects an appropriate device for use in the particular application. The device is selected based upon the size and location of the soft tissue treatment area of the patient. In particular, a device is selected which includes a punctation which is sized and positioned, relative to the contact surface of the device, in such an orientation that when positioned on the soft tissue of the eye, the punctation substantially corresponds to the area to be treated.

Once selected, the device is positioned on the patient's eye so that the punctation corresponds to the area to be treated. Once properly positioned, the iontophoretic administration means is activated and the medicament is iontophoretically administered into the eye of the patient. The orientation means generally maintains the desired orientation of the device relative to the eye of the patient to insure that electric current is properly applied only to the area below the punctation. Similarly, the sealing means precludes the migration of electric current during administration thereof.

Once the administration is complete, the iontophoretic administration means is deactivated. Subsequently, the administrator can remove the device from the eye of the patient. The device is generally discarded upon completion of the treatment, however, it is contemplated that, in certain embodiments, the device may be refilled with medicament.

Figure 3:
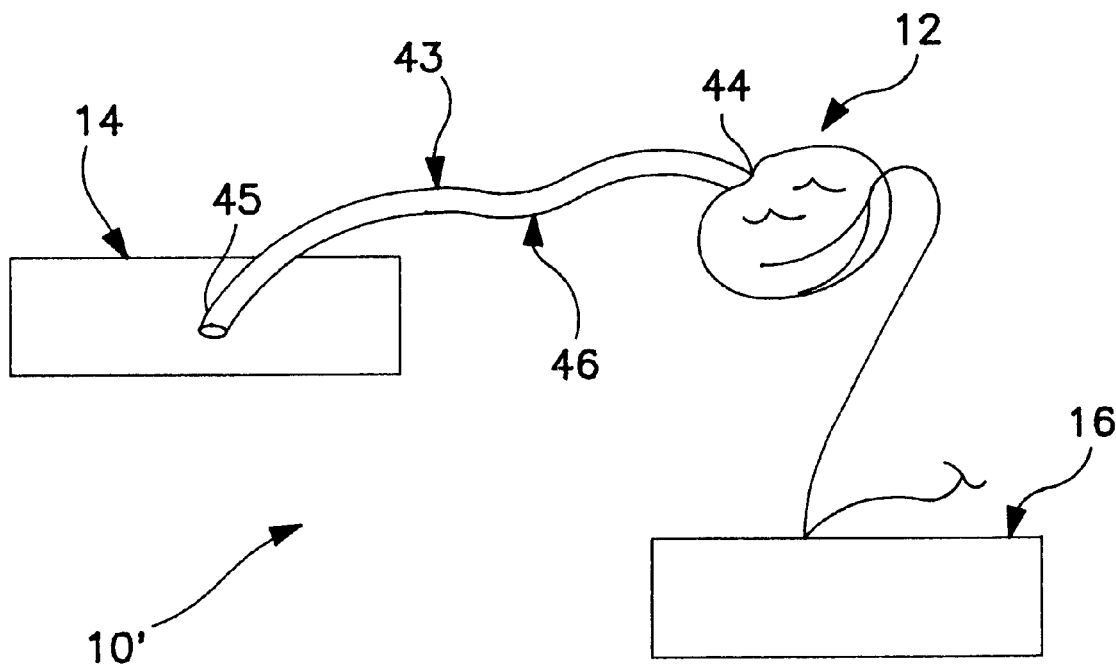
FIG. 3 of the drawings is a schematic view of a second embodiment of the present invention.

Another embodiment of the device is shown generally as 10' in FIG. 3. In such an embodiment, reservoir 12 and applicator 14 are separated by conduit 43. In this embodiment, applicator 14 remains associated with a soft tissue of a patient, however, reservoir 12 is capable of being removed to a remote position relative to applicator 14.

In such an embodiment, conduit 43 comprises first end 44 and second end 45 and length 46 in between. Generally, conduit 43 is associable at first end 44 with reservoir 12 and at second end 45 with the at least one punctation 22 extending through the applicator. Such an association allows the fluid communication of a medicament encompassed within the reservoir with the punctation in the applicator.

Length 46 of conduit 43 is contemplated to be formed in a variety of shapes and tensile strengths. However, preferably the length is formed from a flexible or semi flexible material, such as rubber, plastic and the like, in a cross section that will enable the fluid and constant flow of medicament. For example, a preferred cross section would be circular in shape.

The foregoing description merely explains and illustrates the invention and the invention is not limited thereto except insofar as the appended claims are so limited, as those skilled in the art who have the disclosure before them will be able to make modifications without departing from the scope of the invention.

What is claimed is:

1. A high current density iontophoretic device, comprising:
  a reservoir capable of retaining medicament;
  an applicator, positionable upon a surface of an eye, having at least one punctation therethrough, the at least one punctation capable of being placed in fluid communication with each of the reservoir and at least one treatment area of an eye upon operative positioning of same;
  means for substantially maintaining the orientation of the applicator in the desired orientation upon operative positioning of same; and
  means for iontophoretically administering a medicament from the reservoir to the at least one punctation and, in turn, to an eye of a patient,
  wherein the device further comprises a conduit in fluid communication with both the reservoir and the at least one punctation to, in turn, facilitate the remote positioning of the reservoir relative to the applicator.

2. The device of claim 1, wherein the conduit is of a substantially circular cross section.

3. The device of claim 1, wherein the conduit is formed from a flexible material.

4. A high current density iontophoretic device, comprising:
  a reservoir capable of retaining medicament;
  an applicator, positionable upon a surface of an eye, having at least one punctation therethrough, the at least one punctation capable of being placed in fluid communication with each of the reservoir and at least one treatment area of an eye upon operative positioning of same;
  means for substantially maintaining the orientation of the applicator in the desired orientation upon operative positioning of same; and
  means for iontophoretically administering a medicament from the reservoir to the at least one punctation and, in turn, to an eye of a patient;
  wherein the applicator includes a contact surface, the orientation maintaining means comprising a releasable retaining material associated with the contact surface.

5. The device of claim 4, wherein the releasable retaining material comprises an adhesive.

6. The device of claim 4, wherein the releasable retaining material comprises a lightly crosslinked polymer having a tacky surface configuration.

7. A high current density iontophoretic device, comprising:
  a reservoir capable of retaining medicament, wherein the reservoir includes one of a medicament and a medicament carrier wherein the medicament or medicament carrier comprises a hydrogel medicament carrier;
  an applicator, positionable upon a surface of an eye, having at least one punctation therethrough, the at least one punctation capable of being placed in fluid communication with each of the reservoir and at least one treatment area of an eye upon operative positioning of same;
  means for substantially maintaining the orientation of the applicator in the desired orientation upon operative positioning of same; and
  means for iontophoretically administering a medicament from the reservoir to the at least one punctation and, in turn, to an eye of a patient.

* * * * *